(12) United States Patent
Jung et al.

(10) Patent No.: US 9,049,868 B2
(45) Date of Patent: Jun. 9, 2015

(54) BLUE-GREEN ALGAE REMOVER AND METHOD FOR MANUFACTURING THE SAME

(71) Applicants: Dong-Suek Jung, Seoul (KR); Chil-Soon Pyon, Busan (KR); Hoi-In Jung, Daegu (KR)

(72) Inventors: Dong-Suek Jung, Seoul (KR); Won-Gon Park, Busan (KR)

(73) Assignees: Dong-Suek Jung, Seoul (KR); Chil-Soon Pyon, Busan (KR); Hoi-In Jung, Daegu (KR)

(*) Notice: Subject to any disclaimer, the term of this patent is extended or adjusted under 35 U.S.C. 154(b) by 121 days.

(21) Appl. No.: 14/045,693

(22) Filed: Oct. 3, 2013

(65) Prior Publication Data
US 2015/0099632 A1    Apr. 9, 2015

(51) Int. Cl.
| | |
|---|---|
| *A01N 25/14* | (2006.01) |
| *A01N 59/02* | (2006.01) |
| *A01N 59/06* | (2006.01) |
| *A01N 59/14* | (2006.01) |
| *A01N 59/16* | (2006.01) |
| *C02F 1/50* | (2006.01) |

(52) U.S. Cl.
CPC ............... *A01N 59/16* (2013.01); *A01N 59/02* (2013.01); *A01N 59/14* (2013.01); *A01N 59/06* (2013.01); *A01N 25/14* (2013.01); *C02F 1/50* (2013.01)

(58) Field of Classification Search
CPC .......... C02F 1/50; A01N 25/14; A01N 59/02; A01N 59/06; A01N 59/14; A01N 59/16; A01N 2300/00
See application file for complete search history.

(56) References Cited

U.S. PATENT DOCUMENTS

2008/0103045 A1* 5/2008 Hrdlicka et al. .............. 504/121

FOREIGN PATENT DOCUMENTS

| CN | 103172160 A * | 6/2013 | ............ C02F 1/56 |
|---|---|---|---|
| CN | 103265122 A * | 8/2013 | ............ C02F 3/34 |
| JP | 2008-126159 A | 6/2008 | |
| KR | 10-0386426 B1 | 6/2003 | |
| KR | 10-2006-0103311 A | 9/2006 | |
| KR | 10-0836527 B1 | 6/2008 | |
| KR | 10-1274071 B1 | 6/2013 | |

* cited by examiner

*Primary Examiner* — John Pak
*Assistant Examiner* — Nathan W Schlientz
(74) *Attorney, Agent, or Firm* — Enshan Hong; VLP Law Group LLP

(57) ABSTRACT

Disclosed herein is a blue-green algae remover, including: 0.1 to 1 wt % of sulfuric acid; 2 to 10 wt % of potassium sulfate; 1 to 10 wt % of magnesium sulfate; 1 to 10 wt % of borax; 5 to 40 wt % of zinc sulfate; 1 to 20 wt % of boric acid; and residual water. Since the blue-green algae remover, compared to a conventional blue-green algae remover, is dispersed in water while not being precipitated in water, if it is previously sprayed before the generation of blue-green algae, the generation of blue-green algae can be prevented. Therefore, this blue-green algae remover can also be widely used as an agent for preventing the generation of blue-green algae.

5 Claims, 1 Drawing Sheet

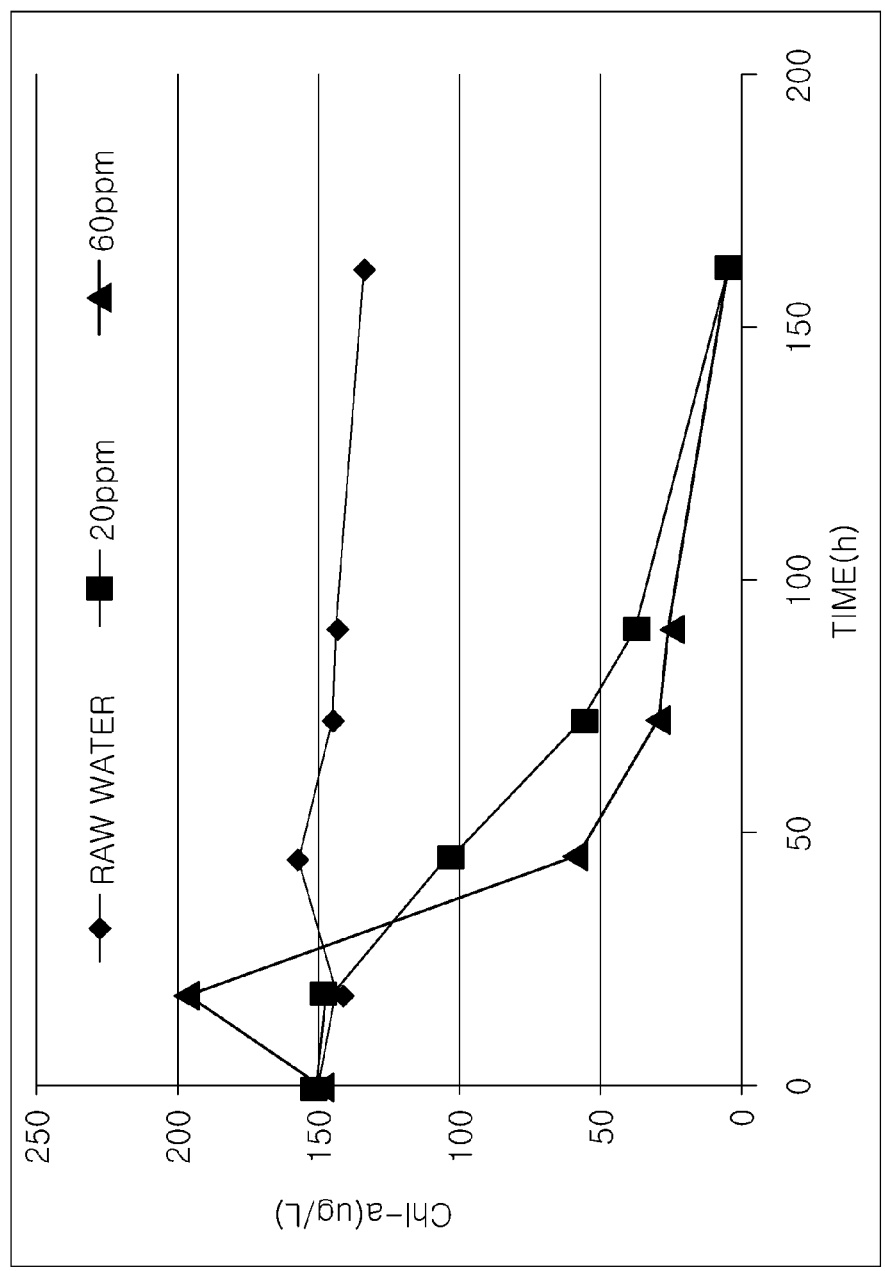

BLUE-GREEN ALGAE REMOVER AND METHOD FOR MANUFACTURING THE SAME

BACKGROUND OF THE INVENTION

1. Technical Field

The present invention relates to a blue-green algae remover and a method of manufacturing the same, and, more particularly, to a blue-green algae remover, which is economical, controls the formation of blue-green algae and has a high efficiency of removing blue-green algae, and to a method of manufacturing the same.

2. Description of the Related Art

Blue-green algae are referred to as algae which do not have a nucleus surrounded by a nuclear membrane and do not have a chloroplast. Blue-green algae are known to cause red tides and green tides. The blue-green algae phenomenon is generally referred to as a phenomenon in which phytoplanktons proliferate in large quantities and live in a river, lake or swamp. Most blue-green algae are flagellates or diatoms. Recently, blue-green algae have been frequently found all over the world, and the concentration thereof has become high.

Excessive supply of nutritive salts (nitrogen and phosphorus) and appropriate water temperature are indicated as the main cause of generation of blue-green algae. Nutritive salts causing the generation of blue-green algae are included in various kinds of feed wastes discharged from sewage, industrial wastewater or farms in large quantities. Once blue-green algae are generated, they rapidly proliferate to cover rivers, dammed water, lakes or the like in an instant, and they secrete viscous liquid to gradually increase the viscosity of the river, so the ecosystem is destroyed, and drinking water for humans and water for agriculture and fishery become dangerous.

Therefore, various research and methods for preventing the generation of blue-green algae have been attempted all over the world. If the inflow of wastewater containing nutritive salts causing the generation of blue-green algae into the river is strictly controlled, the generation of blue-green algae can be effectively prevented, but it is actually difficult to strictly control the inflow of the wastewater into the river.

Accordingly, when blue-green algae are generated, the only real alternative is to try to minimize the damage caused by the blue-green algae. For this purpose, conventionally, when blue-green algae were generated, a blue-green algae inhibitor containing yellow soil or lime as a main ingredient has been sprayed onto the blue-green algae-generated region.

In such a conventional yellow soil spray method, colloid particles of yellow soil agglomerate blue-green algae to precipitate the blue-green algae in water. This method is conducted at low cost, but is problematic in that precipitates float on water or decompose in water to cause secondary environment pollution. Further, this method is not suitable for treating blue-green algae because the actual effectiveness of treating blue-green algae in this way is insignificant.

SUMMARY OF THE INVENTION

Accordingly, the present invention has been made to solve the above-mentioned problems, and an object of the present invention is to provide a blue-green algae remover, which has high removal efficiency and a method of manufacturing the same.

Another object of the present invention is to provide a blue-green algae remover, which can be manufactured at low cost, and a method of manufacturing the same.

Still another object of the present invention is to provide a blue-green algae remover, which can minimize secondary damages, and a method of manufacturing the same.

Still another object of the present invention is to provide a blue-green algae remover, which can prevent the generation of blue-green algae as well as remove the generated blue-green algae, and a method of manufacturing the same.

In order to accomplish the above objects, an aspect of the present invention provides a blue-green algae remover, including: 0.1 to 1 wt % of sulfuric acid; 2 to 10 wt % of potassium sulfate; 1 to 10 wt % of magnesium sulfate; 1 to 10 wt % of borax; 5 to 40 wt % of zinc sulfate; 1 to 20 wt % of boric acid; and residual water.

The blue-green algae remover may be manufactured in the form of dry powder in terms of transportation and storage.

Another aspect of the present invention provides a method of manufacturing a blue-green algae remover, including the steps of: a) mixing 10 to 50 wt % of water and 0.1 to 1 wt % of sulfuric acid and then stirring the mixture in a reaction tank to prepare a sulfuric acid solution; b) dissolving 2 to 10 wt % of potassium sulfate, 1 to 10 wt % of magnesium sulfate, 1 to 10 wt % of borax, 5 to 40 wt % of zinc sulfate and 1 to 20 wt % of boric acid in the sulfuric acid solution to form a mixed solution and then aging the mixed solution for a predetermined amount of time; and c) filtering the mixed solution aged in the step b).

The method may further include the step of obtaining a powdered composition by concentrating and/or crystallizing the liquid blue-green algae remover.

In the method, the obtaining the powdered composition may include the steps of: d) heating the mixed solution filtered in the step c) to concentrate the mixed solution; e) crystallizing the mixed solution concentrated in the step d) to obtain a crystalline product; and f) dewatering and drying the crystalline product.

BRIEF DESCRIPTION OF THE DRAWINGS

The above and other objects, features and advantages of the present invention will be more clearly understood from the following detailed description taken in conjunction with the accompanying drawing, in which:

FIG. 1 is a graph showing the effect of removing blue-green algae from raw water containing the blue-green algae remover of the present invention according to the time.

DESCRIPTION OF THE PREFERRED EMBODIMENTS

Hereinafter, preferred embodiments of the present invention will be described in detail.

Chemical Composition

The blue-green algae remover of the present invention includes 0.1 to 1 wt % of sulfuric acid, 2 to 10 wt % of potassium sulfate, 1 to 10 wt % of magnesium sulfate, 1 to 10 wt % of borax, 5 to 40 wt % of zinc sulfate, 1 to 20 wt % of boric acid, and residual water.

Sulfuric Acid: 0.1 to 1 wt %

Sulfuric acid is mixed with water, and is added in order to induce the reaction between the components of the blue-green algae remover. According to an embodiment of the present invention, sulfuric acid may be included in an amount of 0.1 to 1 wt %.

Potassium Sulfate: 2 to 10 wt %

Potassium sulfate is used in decomposing a nitrogen component causing the generation of blue-green algae. According to an embodiment of the present invention, potassium sulfate may be included in an amount of 2 to 10 wt %. When the amount thereof is less than 2 wt %, the input effect thereof is insufficient. When the amount thereof is more than 10 wt %, the input effect thereof is not further improved.

Magnesium Sulfate: 1 to 10 wt %

Magnesium sulfate: magnesium (Mg) comes into contact with water to be converted into magnesium hydroxide, and then magnesium hydroxide is dissociated into magnesium ions ($Mg^{2+}$) and hydroxide ions (OH), and then magnesium ions ($Mg^{2+}$) and hydroxide ions ($OH^-$) react with a phosphate group (major prey of blue-green algae) according to the following Reaction Formula 1 to prepare inactive magnesium phosphate. According to an embodiment of the present invention, magnesium sulfate may be included in an amount of 1 to 10 wt %. When the amount thereof is more than 10 wt %, an increase in the efficiency of removing blue-green algae is low, whereas other functionalities become insufficient.

$$5Mg+20H+3PO_4 \rightarrow Mg_5(OH)(PO_4)_3 (\text{inactive}) \quad (1)$$

Borax: 1 to 10 wt %

Borax is used as a disinfectant, and serves to prevent water from being decayed by supplying oxygen to the water containing blue-green algae. According to an embodiment of the present invention, borax may be included in an amount of 1 to 10 wt %.

Zinc Sulfate: 5 to 40 wt %

Zinc sulfate is used in destroying blue-green algae. According to an embodiment of the present invention, zinc sulfate may be included in an amount of 5 to 40 wt %.

Boric Acid: 1 to 20 wt %

Boric acid is applied to a disinfectant for bacteria. In the blue-green algae remover of the present invention, boric acid is used in preventing blue-green algae decomposed in water from being converted into secondary bacteria. According to an embodiment of the present invention, boric acid may be included in an amount of 1 to 20 wt %. When the amount thereof is more than 20 wt %, there is no further improvement in sterilizing power, whereas other functionalities are deteriorated.

When the blue-green algae remover having the above composition is sprayed in a concentration of 5 to 40 ppm, very high removal effect can be obtained. Further, when the blue-green algae remover is sprayed just before the generation of blue-green algae, the generation of blue-green algae can be prevented for 15 days or more. Particularly, when the blue-green algae remover is sprayed in advance, the cost for removing blue-green algae can be reduced by 30 to 50% due to the decrease in the amount of the blue-green algae remover to be sprayed.

Manufacturing Method

The blue-green algae remover of the present invention is manufactured by mixing and stirring water and sulfuric acid to prepare a sulfuric acid solution, dissolving magnesium sulfate, potassium sulfate, zinc sulfate and borax in the sulfuric acid solution to prepare a mixed solution and then filtering the mixed solution. Hereinafter, the method of manufacturing a blue-green algae remover according to the present invention will be described in more detail.

In order to manufacture the blue-green algae remover of the present invention, first, 10 to 50 wt % of water and 0.1 to 1 wt % of sulfuric acid were mixed and stirred to prepare a sulfuric acid solution.

Subsequently, 2 to 10 wt % of potassium sulfate, 1 to 10 wt % of magnesium sulfate, 1 to 10 wt % of borax, 5 to 40 wt % of zinc sulfate and 1 to 20 wt % of boric acid were dissolved in the sulfuric acid solution to prepare a mixed solution, and then the mixed solution is aged. The aging time may be 30 to 50 minutes.

Next, the aged mixed solution is filtered to remove impurities.

The blue-green algae remover manufactured by this method has a liquid form.

Meanwhile, since a liquid composition is not easy to transport or store compared to a powdered composition, the liquid composition may be directly transported to a nearby place, but is required to be powdered in order for it to be easily transported and stored when it is to be transported to a distance place. Thus, according to another embodiment of the present invention, there is provided a method of manufacturing a powdered blue-green algae remover by concentrating and/or crystallizing the liquid blue-green algae remover. Hereinafter, this method will be described in detail.

In order to manufacture a powdered blue-green algae remover, the liquid blue-green algae remover, from which impurities were removed by filtering, is heated and concentrated at 100 to 130° C. to be evaporated. In this case, the powdered blue-green algae remover may be manufactured by evaporating the liquid blue-green algae remover and then drying it or by partially evaporating the liquid blue-green algae remover and then crystallizing it. Further, a crystalline product is obtained by vacuum concentration.

In the crystallization procedure for manufacturing the powdered blue-green algae remover, a blue-green algae remover solution is shifted from a reaction tank to a crystallization tank, and is then maintained at 1 to 10° C. to obtain a $7H_2O$-containing crystalline product.

The obtained $7H_2O$-containing crystalline product is dewatered by a centrifugal separator, and is then dried at 120 to 150° C. to obtain a powdered blue-green algae remover.

The powdered blue-green algae remover is stored as a powder. At the time of removing blue-green algae, 450 to 500 kg of the powdered blue-green remover is dissolved in 1,000 kg of water and is then sprayed in a concentration of 5~20 ppm.

EXAMPLE 1750 kg of water and 250 kg of sulfuric acid were mixed and stirred in a reaction tank to prepare a sulfuric acid solution. Subsequently, 800 kg of magnesium sulfate, 700 kg of potassium sulfate, 4000 kg of zinc sulfate, 1000 kg of borax and 1500 kg of boric acid were dissolved in the sulfuric acid solution to form a mixed solution, and then the mixed solution was aged for 30 to 50 minutes. Subsequently, the aged mixed solution was filtered to remove impurities, and was then heated and concentrated at 120 to 130° C. to be evaporated. Then, the mixed solution concentrated by evaporation was shifted to a crystallization tank, and was then crystallized at 1 to 10° C. to obtain a $7H_2O$-containing crystalline product. Then, the obtained $7H_2O$-containing crystalline product was dewatered by a centrifugal separator, and was then dried at 120 to 150° C. to obtain about 4500 kg of a powder product.

FIG. 1 is a graph showing the results of observing the effect of removing blue-green algae from raw water according to the time, wherein the raw water contains microcystic as blue-green algae in an initial concentration of 150 μg/L, and the blue-green algae remover according to an embodiment of the present invention was injected into the raw water in concentrations of 20 ppm and 40 ppm, respectively. As shown in FIG. 1, it can be ascertained that, in the case of the raw water (Comparative Example) containing no blue-green algae remover of the present invention, the concentration of blue-green algae was not changed ever after 160 hours (6.8 days), but that, in the case of the raw water containing the blue-green algae remover of the present invention in a concentration of 20 ppm, the concentration of blue-green algae was gradually decreased with the passage of time, and blue-green algae was completely removed from the raw water after 160 hours. Further, it can be ascertained that, in the case of the raw water containing the blue-green algae remover of the present invention in a concentration of 40 ppm, the removal efficiency of blue-green algae is higher compared to in the case of the raw water containing the blue-green algae remover of the present invention in a concentration of 20 ppm.

As described above, the blue-green algae remover manufactured by the method of the present invention has a low production cost and has excellent effects of preventing the generation of blue-green algae and removing blue-green algae. Further, since the blue-green algae remover of the present invention, compared to a conventional blue-green algae remover, is dispersed in water while not being precipitated in water, if it is previously sprayed before the generation of blue-green algae, the generation of blue-green algae can be prevented. Therefore, this blue-green algae remover can also be widely used as an agent for preventing the generation of blue-green algae.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A blue-green algae remover, comprising: 0.1 to 1 wt % of sulfuric acid; 2 to 10 wt % of potassium sulfate; 1 to 10 wt % of magnesium sulfate; 1 to 10 wt % of borax; 5 to 40 wt % of zinc sulfate; 1 to 20 wt % of boric acid; and the remainder water.

2. A blue-green algae removing dry powder obtained by preparing a solution comprising 0.1 to 1 wt % of sulfuric acid, 2 to 10 wt % of potassium sulfate, 1 to 10 wt % of magnesium sulfate, 1 to 10 wt % of borax, 5 to 40 wt % of zinc sulfate, 1 to 20 wt % of boric acid, and water followed by concentrating and/or crystallizing the solution to obtain a dry powder.

3. A method of manufacturing a blue-green algae remover, comprising:
   a) mixing water and sulfuric acid and then stirring the mixture in a reaction tank to prepare a sulfuric acid solution;
   b) dissolving potassium sulfate, magnesium sulfate, borax, zinc sulfate and boric acid in the sulfuric acid solution to form a mixed solution comprising 10 to 50 wt % of water, 0.1 to 1 wt % of sulfuric acid, 2 to 10 wt % of potassium sulfate, 1 to 10 wt % of magnesium sulfate, 1 to 10 wt % of borax, 5 to 40 wt % of zinc sulfate and 1 to 20 wt % of boric acid, and then aging the mixed solution for 30 to 50 minutes; and
   c) filtering the mixed solution aged in the step b).

4. The method of claim 3, further comprising obtaining a powdered composition by concentrating and/or crystallizing the solution obtained in step c).

5. The method of claim 4, wherein the obtaining the powdered composition comprises:
   d) heating the mixed solution filtered in the step c) to concentrate the mixed solution;
   e) crystallizing the mixed solution concentrated in the step d) to obtain a crystalline product; and
   f) dewatering and drying the crystalline product.

* * * * *